(12) United States Patent
Ten Kate et al.

(10) Patent No.: US 11,919,866 B2
(45) Date of Patent: Mar. 5, 2024

(54) PROCESS FOR PREPARING CYCLIC ALKYLENE UREAS

(71) Applicant: NOURYON CHEMICALS INTERNATIONAL B.V., Arnhem (NL)

(72) Inventors: Antoon Jacob Berend Ten Kate, Arnhem (NL); Karl Fredrik Lake, Södertälje (SE); Michiel Jozef Thomas Raaijmakers, Deventer (NL); Rolf Krister Edvinsson, Partille (SE); Jenny Valborg Therese Adrian Meredith, Årsta (SE); Rens Veneman, Amersfoort (NL); Hendrik Van Dam, Ede (NL); Eike Nicolas Kantzer, Uddevalla (SE); Ina Ehlers, Stenungsund (SE); Slavisa Jovic, Utrecht (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/638,347

(22) PCT Filed: Aug. 7, 2018

(86) PCT No.: PCT/EP2018/071325
§ 371 (c)(1),
(2) Date: Feb. 11, 2020

(87) PCT Pub. No.: WO2019/030195
PCT Pub. Date: Feb. 14, 2019

(65) Prior Publication Data
US 2020/0223800 A1  Jul. 16, 2020

(30) Foreign Application Priority Data
Aug. 11, 2017 (EP) ..................... 17186004

(51) Int. Cl.
C07D 233/34 (2006.01)
(52) U.S. Cl.
CPC .................. C07D 233/34 (2013.01)
(58) Field of Classification Search
CPC ................................................ C07D 233/34
See application file for complete search history.

(56) References Cited

U.S. PATENT DOCUMENTS

| | | | |
|---|---|---|---|
| 2,436,311 A | 2/1948 | Larson et al. | |
| 2,517,750 A | 8/1950 | Wilson | |
| 2,613,212 A | 10/1952 | Hurwitz et al. | |
| 2,812,333 A | 11/1957 | Steele | |
| 4,387,249 A | 6/1983 | Harnden et al. | |
| 4,405,794 A | 9/1983 | Harnden et al. | |
| 4,503,250 A | 3/1985 | Herdle | |
| 4,514,379 A | 4/1985 | Miller | |
| 4,642,351 A | 2/1987 | Woo et al. | |
| 4,650,906 A | 3/1987 | Murakami et al. | |
| 4,683,337 A | 7/1987 | Budde | |
| 8,513,435 B2 | 8/2013 | Baloche et al. | |
| 9,440,928 B2 | 9/2016 | Gupta et al. | |
| 9,475,780 B2 | 10/2016 | Gupta et al. | |
| 10,428,011 B2* | 10/2019 | Edvinsson | ........ C07C 273/1809 |
| 10,844,001 B2* | 11/2020 | Edvinsson | ........ C07C 273/1836 |

(Continued)

FOREIGN PATENT DOCUMENTS

| CN | 102686567 A | 9/2012 |
|---|---|---|
| CN | 103732579 A | 4/2014 |

(Continued)

OTHER PUBLICATIONS

EPO, European Extended Search Report issued in European Application No. 17186004.2, dated Feb. 9, 2018.

(Continued)

*Primary Examiner* — Rebecca L Anderson
(74) *Attorney, Agent, or Firm* — LORENZ & KOPF, LLP

(57) ABSTRACT

A process for producing a cyclic alkylene urea product of Formula I:

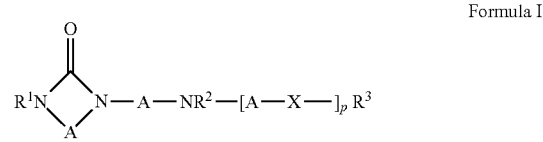

Formula I in which a compound of Formula II and/or Formula III is contacted in a reaction zone with a compound of Formula IV and/or Formula V and in the presence of one or more carbonyl delivering compounds;

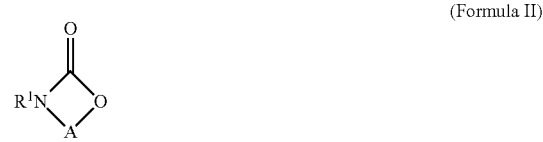

(Formula II)

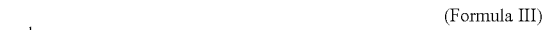

(Formula III)

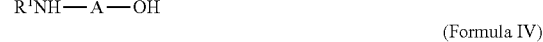

(Formula IV)

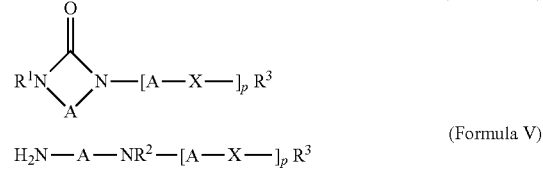

(Formula V)

wherein the compound of Formula II and/or the compound of Formula III are added to a reaction zone comprising compound of Formula IV and/or compound of Formula (V) continuously or semi-continuously over a period of time, or in two or more batches.

10 Claims, 1 Drawing Sheet

(56) References Cited

U.S. PATENT DOCUMENTS

| | | |
|---|---|---|
| 2013/0023667 A1 | 1/2013 | Baloche et al. |
| 2014/0179931 A1 | 6/2014 | Gupta et al. |
| 2019/0031597 A1 | 1/2019 | Edvinsson et al. |

FOREIGN PATENT DOCUMENTS

| | | | |
|---|---|---|---|
| CN | 103732580 A | 4/2014 | |
| JP | S60120842 A | 6/1985 | |
| JP | S60126248 A | 7/1985 | |
| JP | H0641023 A | 2/1994 | |
| JP | H0665160 A | 3/1994 | |
| JP | 200018607 A | 7/2000 | |
| JP | 2000186074 A | 7/2000 | |
| JP | 2003212855 A | 7/2003 | |
| JP | 2019504844 A | 2/2019 | |
| RU | 2471775 C1 | 1/2013 | |
| WO | WO-2017137532 A1 * | 8/2017 | ........... C07C 209/16 |

OTHER PUBLICATIONS

EPO, International Search Report and Written Opinion issued in International Application No. PCT/EP2018/071325, dated Oct. 8, 2018.

\* cited by examiner

EDA
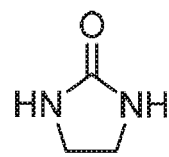
EU
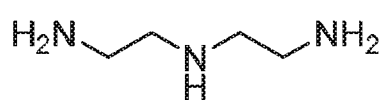
DETA
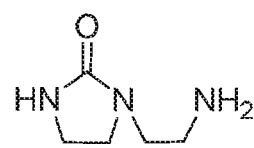
UDETA
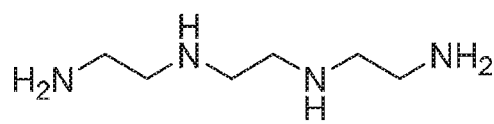
L-TETA
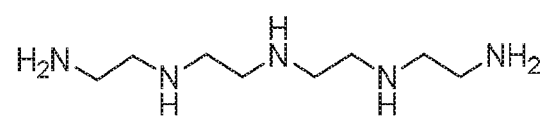
L-TEPA
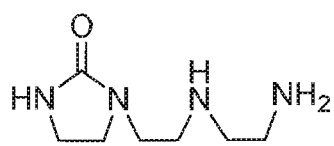
U1TETA
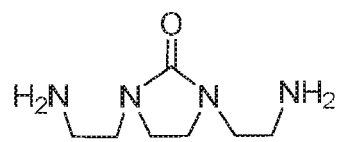
U2TETA
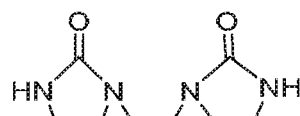
DUTETA
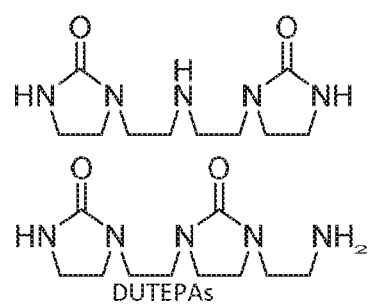
DUTEPAs

PROCESS FOR PREPARING CYCLIC ALKYLENE UREAS

CROSS-REFERENCE TO RELATED APPLICATION

This application is a U.S. National-Stage entry under 35 U.S.C. § 371 based on International Application No. PCT/EP2018/071325, filed Aug. 7, 2018, which was published under PCT Article 21(2) and which claims priority to European Application No. 17186004.2, filed Aug. 11, 2017.

TECHNICAL FIELD

The invention is directed to a process for preparing cyclic alkylene ureas, in particular to a method for controlling the production of cyclic alkylene ureas and alkylene alcohol-substituted ureas, which can be used in the production of various alkylene amines.

BACKGROUND

Aqueous solutions of alkyleneamines and alkanolamines are often used in reversible CO2 absorption processes. On absorption, a range of compounds are formed, such as carbonates, bicarbonates, carbamates and alkylene ureas. Desired products are those that readily desorb CO2 on heating. Cyclic carbamates and ureas are generally considered undesirable owing to their high stability.

U.S. Pat. No. 4,650,906 and JP 60126248 disclose decarboxylation of ethylene amine carbonates by heat treatment and distillation. Examples of carbonates disclosed are those of diethylenetriamine (DETA), triethylenetetramine (TETA), tetraethylenepentamine (TEPA), pentaethylenehexamine (PEHA) and piperazine (PIP). JP 60120842 discloses, in addition to thermal treatment, the addition of a hydroxide-containing base. None of these documents disclose cyclic alkylene ureas or their conversion to corresponding alkyleneamines.

U.S. Pat. No. 4,683,337 discloses the conversion of ethyleneamines to linear carbamates by reacting them with CO2 followed by decarbonating and dehydrating them to recover the amines. It does not disclose the formation of cyclic alkylene ureas.

U.S. Pat. No. 4,387,249 discloses the reaction of ethylenediamine (EDA), ethanolamine (MEA) and urea to give aminoethylethyleneurea (UDETA) and ethyleneurea (EU) which, after hydrolysis, gives DETA and EDA. The hydrolysis is said to be done in the presence of a Brønsted base, although the only one specifically mentioned is sodium hydroxide.

U.S. Pat. No. 4,503,250 discloses the hydrolysis of a product mixture obtained by the reaction of an amine or ammonia with an alcohol in the presence of carbonic acid derivatives. In the examples, work-up of the reaction mixture is performed using 50% aqueous KOH under reflux overnight. The yield of alkylene amines obtained by treating the reaction mixture with KOH is low.

US 2014/0179931 describes a process for producing N-substituted cyclic alkylene ureas from multifunctional aliphatic amines with at least two amino groups, and an aliphatic organic carbonate, preferably in the presence of a basic catalyst such as an alkali or alkaline earth metal alkoxide.

U.S. Pat. No. 4,405,794 relates to a method for reacting urea and beta-hydroxyethylcarbamate to make 2-oxazolidinone (CMEA) and ethyleneurea.

US 2013/0023667 describes the formation of aminoethylimidazolidinone (UDETA) by reacting diethylenetriamine (DETA) with urea.

U.S. Pat. No. 2,517,750 describes the production of 2-imidazolidinone (EU) and N-substituted derivatives from urea and ethylene amines including EDA, DETA, linear TETA (L-TETA), aminoethylethanolamine (AEEA), and aminoethyl aniline.

U.S. Pat. No. 2,436,311 relates to the production of ethylene urea (EU) from urea and alpha-beta-substituted ethylenic compounds such as ethylene glycol, ethylenediamine (EDA) or ethanolamine (MEA).

U.S. Pat. No. 4,514,379 describes the conversion of oxidazolidinones to alkanol amine and CO2 in the presence of a catalytic amount of an amine, preferably the alkanol amine precursor to the oxazolidinone.

U.S. Pat. No. 2,812,333 describes a process for the preparation of N-(2-hydroxyethyl) ethylene diamine by reacting 2-aminoethanol with carbon dioxide at elevated temperature and pressure to yield 1-(2-hydroxyethyl) imidazolidone-2, which is subsequently hydrolysed to form N-(2-hydroxyethyl) ethylene diamine.

There remains a need for an alternative process for producing cyclic amines, in a way which can improve control, for example in reactant conversions and/or improved product selectivity.

In addition, other objects, desirable features and characteristics will become apparent from the subsequent summary and detailed description, and the appended claims, taken in conjunction with the accompanying drawings and this background.

SUMMARY

A process is provided for producing a cyclic alkylene urea product from an alkyleneamine and/or cyclic alkylene urea reactant and an alkanolamine and/or cyclic alkylene carbamate reactant, wherein the cyclic alkylene carbamate reactant and/or the alkanolamine reactant are added to a reaction zone comprising a cyclic alkylene urea reactant and/or an alkylene amine reactant continuously, semi-continuously, or in two or more batches.

The cyclic alkylene urea product is of Formula I:

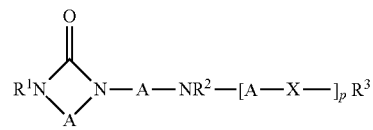

Formula I

The cyclic alkylene carbamate reactant is selected from compounds of Formula II:

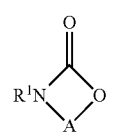

Formula II

The alkanolamine reactant is selected from compounds of Formula III:

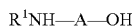 

R¹NH—A—OH    Formula III

The cyclic alkylene urea reactant is selected from compounds of Formula IV:

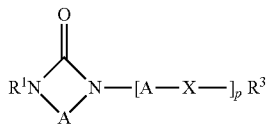

Formula IV

The alkyleneamine reactant is selected from compounds of Formula V:

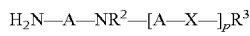

Formula V

In the above formulae, $R^1$ is $—[A—X—]_q R^3$;

$R^2$ is on each occurrence independently selected from H and $C_1$ to $C_6$ alkyl groups which are optionally substituted by one or two groups selected from $—OH$ and $—NH_2$;

$R^3$ is on each occurrence independently selected from H and $C_1$ to $C_6$ alkyl groups which are optionally substituted by one or two groups selected from $—OH$ and $—NH_2$;

A is on each occurrence independently selected from $C_1$ to $C_3$ alkylene units, optionally substituted by one or more $C_1$ to $C_3$ alkyl groups;

X is on each occurrence independently selected from $—O—$, $—NR^2—$, groups of Formula VI, and groups of Formula VII:

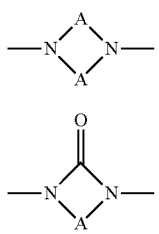

Formula VI

Formula VII and;

p and q are each independently selected from a whole number in the range of from 0 to 8.

In the process of the invention, improved control, for example in reactant conversions and/or improved product selectivity, is achieved by adding the cyclic alkylene carbamate reactant of Formula II and/or the cyclic alkanolamine reactant of Formula III to the cyclic alkylene urea reactant of Formula IV and/or alkyleneamine reactant of Formula V continuously or semi-continuously over a period of time, or intermittently in two or more batches. Thus, even using the same total amount of reactants, adding the compound of Formula II and/or III over a period of time (continuously, semi-continuously or in batches) can achieve improved overall conversions and/or improved product selectivity. The latter feature may be of particular importance. Batches may have the same size or have different sizes. As will be evident, a batch which is present at the start of the reaction also counts as a batch.

The reaction is carried out in the presence of at least one carbonyl delivering agent. The carbonyl delivering agent can, in embodiments, be the cyclic alkylene carbamate reactant of Formula II or the cyclic alkylene urea reactant of Formula IV.

BRIEF DESCRIPTION OF DRAWINGS

The present invention will hereinafter be described in conjunction with the following drawing FIGURES, wherein like numerals denote like elements, and:

FIG. 1 shows structures of compounds referred to in the description.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description.

The cyclic alkylene carbamate reactant of Formula II can be used in the production of cyclic alkylene urea products of Formula I when contacted with an alkylene amine compound of Formula V.

The cyclic alkylene carbamate reactant compounds can be added directly to the reaction zone, or they can form in situ from an alkanol amine reactant of Formula III in the presence of a carbonyl delivering agent.

The alkylene amine reactant of Formula V can be added directly to the reaction zone, or it can alternatively be formed in situ from a cyclic alkylene urea reactant compound of Formula IV.

In the presence of a carbonyl delivering agent, alkanol amine reactant of Formula III can form a cyclic alkylene carbamate reactant of Formula II, and an alkylene (di)amine reactant of Formula V can form a cyclic alkylene urea reactant of Formula IV.

In embodiments, the reaction is controlled by ensuring that the total amount of cyclic alkylene carbamate reactant of Formula II and alkanol amine reactant of Formula III added to the reaction zone does not exceed (on a molar basis) a predetermined level compared to the amount of reactant of Formula IV and compound of Formula V that are present initially. After the reaction has proceeded for some time, a second addition of reactants of Formula II and/or Formula III can be added, again such that the amount added does not exceed the predetermined level. Further batches can be similarly added. In embodiments, this predetermined level that is not exceeded is 0.60. In further embodiments, this predetermined level that is not exceeded is 0.45, for example 0.40 or 0.35. In other embodiments, the predetermined level does not exceed 0.30, 0.25, 0.20 or 0.16. In certain embodiments, numbers in this description indicating amounts, ratios of materials, physical properties of materials, and/or use are may be understood as being modified by the word "about". The term "about" as used in connection with a numerical value and the claims denotes an interval of accuracy, familiar and acceptable to a person skilled in the art. In general, such interval of accuracy is ±10%.

In embodiments, the value of t can be 30, 60 or 90 minutes. This means that the predetermined level is calculated such that the total amount of compound of Formula II and/or Formula III added over the allocated time period does not exceed the predetermined level based on the initial amounts of compound of Formula IV and/or V that were present in the reaction zone.

Operating under conditions where the predetermined level is not exceeded can further improve yields of the desired cyclic alkylene urea products (of Formula I), and corresponding alkylene amines that result from their decarbonylation (of Formula IX).

The reaction zone comprises at least one carbonyl delivering agent. The carbonyl (CO) delivering agent is a compound containing a carbonyl moiety that can be transferred to an alkanolamine or alkylene diamine compound leading to the formation of, respectively, a cyclic alkylene carbamate or a cyclic alkylene urea. Examples of carbonyl delivering agents include carbon dioxide, and organic compounds in which a carbonyl moiety is available for being transferred as described above. Organic compounds in which a carbonyl moiety is available include urea and derivatives thereof; linear and cyclic alkylene ureas, especially cyclic urea, mono or di-substituted alkylene ureas, alkyl and dialkyl ureas, linear and cyclic carbamates, organic carbonates and derivatives or precursors thereof. Such derivatives or precursors may for example include ionic compounds such as carbonate or bicarbonate salts, carbamic acids, that can be converted, in some embodiments in situ in the process of the invention, into their non-ionic counterparts, for example into linear and cyclic carbamate or urea compounds. When such ionic compounds are used in the present invention, they are organic hydrocarbon-based carbonate or bicarbonate salts. Preferably the CO delivering agent is $CO_2$ or an organic compound that is suitable for use as a carbon oxide delivering agent, for example a cyclic carbamate, such as a cyclic alkylene carbamate reactant of Formula II, or a cyclic urea, such as a cyclic alkylene urea reactant of Formula IV. In embodiments, the alkylene is ethylene. In other embodiments, the carbon dioxide delivering agent is urea or ethylene carbonate.

Thus, carbonyl delivering agent can in embodiments be selected from carbon dioxide; inorganic carbonic acid salts; cyclic and non-cyclic carbonic acid esters; urea; optionally substituted alkyl ureas; optionally substituted cyclic alkylene ureas; carbamic acids; carbamic acid salts; and cyclic and non-cyclic carbamic acid esters.

In further embodiments, the carbonyl delivering agent is selected from carbon dioxide, urea, cyclic alkylene carbonates, cyclic alkylene carbamates and cyclic alkylene ureas. In preferred embodiments, the cyclic alkylene carbamate reactant of Formula II and/or the cyclic alkylene urea reactant of Formula IV can act as the carbonyl delivering agent.

In embodiments, a cyclic alkylene carbamate reactant of Formula II can be produced from an alkanolamine reactant of Formula III by heating in the presence of a carbonyl delivering agent, e.g. a cyclic alkylene urea of Formula IV.

Additional reactants of Formula IV and/or Formula V can be added to the reaction zone once their initial quantity has depleted. In this case, the molar ratio calculations set out above (i.e. of the predetermined level of reactants of Formula II and/or III to the reactants of Formula IV and/or V, and the molar ratio of carbonyl delivering compounds to the reactants of Formula IV and/or Formula V) are based not only on the amounts of additional reactants added, but also the residual amounts of the reactants present in the reaction zone before addition of fresh reactants. Thus, as an example, if the reaction zone comprises 0.1 mol reactant of Formula II, 0.2 mol reactant of Formula III, 0.3 mol reactant of Formula IV and 0.4 mol reactant of Formula V, and an additional 0.5 mol of reactant of Formula IV is added, then the predetermined ratio would be calculated based on a total of 1.2 mol reactants of Formula IV and V being present (i.e. 0.3+0.4+0.5 mol). In addition, any additional reactants of Formula II and/or Formula III being added would have to take into account that 0.3 mol of these reactants already exists in the reaction zone.

Thus, the calculation of the predetermined level can be based on the following equation:

$$PL(t) = \frac{N(II, III) + rN(II, III)}{N(IV, V) + rN(IV, V)}$$

In this equation:
PL(t)=the predetermined level over a time period of t minutes
N(II,III)=total moles of reactant of Formula II and Formula III that can be added over time period (t)
rN(II,III)=total residual moles of reactant of Formula II and Formula III that are present in the reaction zone before addition of fresh reactants of Formula IV and/or Formula V
N(IV,V)=total moles of reactant of Formula IV and/or Formula V that are added to the reaction zone
rN(IV,V)=total residual moles of reactant of Formula IV and Formula V that are present in the reaction zone before addition of fresh reactants of Formula IV and/or Formula V As explained above, the process can be operated such that the specified PL(t) value is not exceeded. In embodiments PL can be 0.45, 0.40, 0.35, 0.30, 0.25, 0.20 or 0.16, and t can be 30 minutes, 60 minutes or 90 minutes. Thus, in embodiments, PL(30) does not exceed 0.45, 0.35, 0.30, 0.25, 0.20 or 0.16; or in other embodiments, PL(60) does not exceed 0.45, 0.35, 0.30, 0.25, 0.20 or 0.16; or, in further embodiments, PL(90) does not exceed 0.45, 35, 0.30, 0.25, 0.20 or 0.16.

With respect to the molecular formulae, in embodiments group A in each case is independently selected from optionally substituted $C_2$-$C_3$ alkylene groups cases. In further embodiments, A in all cases is an ethylene group (i.e. $C_2$ alkylene).

In embodiments, each R2 is selected from H and C1 to C3 alkyl (e.g. C2 alkyl) optionally substituted with one $NH_2$ or OH group. Where there is a substituent, it is preferably an NH2 group.

In embodiments, each R3 is selected from H and C1 to C3 alkyl (e.g. C2 alkyl) optionally substituted with one NH2 or OH group. Where there is a substituent, it is preferably an NH2 group. In embodiments, R3 is hydrogen.

In embodiments, p is 6 or less. In further embodiments, p is zero, 1 or 2. In other embodiments, mixtures of products can form having different values of p.

In embodiments, q is 6 or less. In further embodiments, q is zero, 1 or 2, preferably zero or 1.

In embodiments, no more than one X group is a cyclic moiety selected from groups of Formula VI and Formula VII.

In embodiments, the alkanolamine reactant is monoethanolamine (MEA) and/or the cyclic alkylene carbamate reactant is 2-oxazolidinone (CMEA). In embodiments, the alkyleneamine reactant is ethylenediamine (EDA) and/or the cyclic alkylene urea reactant is ethyleneurea (EU). The product where these reactants are used is 1-(2-aminoethyl) imidazolidin-2-one (UDETA), which can be decarbonylated to form diethylenetriamine (DETA). Higher ethylene amines can be formed through reaction of DETA with the cyclic alkylene carbamate reactant of Formula II (e.g. CMEA) and/or alkanolamine reactant of Formula III.

It has been found that controlling the rate of addition of compound of Formula II and/or Formula III, the yield of the cyclic alkylene urea product of Formula I can be improved. Thus, by adding the cyclic alkylene carbamate reactant and/or alcoholamine reactant continuously over a period of time, or in two or more batches during the course of the reaction, yields can be improved compared to addition of all reactants of Formula II and/or Formula III at once at the beginning of the reaction.

Yields can also be improved by controlling the ratio of reactants of Formula II and/or III compared to the amount of reactants of Formula IV and/or V to below a predetermined level. Without being bound by theory, it is believed that this is achieved by reducing the ability of a competing reaction to proceed, which diverts reactant of Formula II and/or III into producing a 2-hydroxyalkyl-substituted cyclic alkylene urea of Formula VIII:

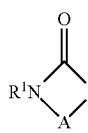

Formula VIII

The reaction zone is typically any suitable reactor including a continuously stirred tank reactor, a pipeline reactor, or a tubular or multi-tubular reactor. The reactor may be adiabatic or equipped with external or internal heating devices. Reactants can be fed through a single point or split into multiple feed-points. The reaction zone can consist of multiple reactor stages with inter-stage heat exchange.

The reaction zone is preferably maintained at a temperature of at least 100° C. The temperature should preferably be lower than 400° C. More preferably the temperature is between 200 and 360° C. Even more preferably the temperature is between 230 and 340° C., for example between 230 and 290° C. Most preferably the temperature is between 250 and 310° C. In embodiments where the alkanolamine reactant is monoethanolamine the most preferred temperature range is between 230 and 290° C.

The reaction zone is preferably maintained at a pressure of from 1 to 100 bar absolute. Preferably, the pressure is from 5 to 70 bar absolute, for example 10 to 50 bar absolute.

The reaction time during the process is, in embodiments, between 5 minutes and 15 hours, preferably between 0.5 and 10 hours, more preferably between 1 and 6 hours.

The process can be carried out in one or multiple batch reactors, and/or in a continuously operating system in one reactor or in a cascade of continuous flow reactors, optionally with multiple feeding points. The reaction and separation can be performed in separate steps or at least partially simultaneously. The reaction and separation can involve multiple reaction steps with separation steps in between.

The person skilled in the art is capable of selecting the proper reactor and separation unit scheme by determining the overall yield, energy consumption and waste production.

The process can be carried out in the presence of a solvent, such as water or an alcohol. If a solvent is to be used, water is preferred.

The process can comprise decarbonylating the cyclic alkylene urea product to produce an alkyleneamine of Formula IX:

Formula IX

The decarbonylation can occur to some extent in situ, without a specific decarbonylation step. Thus the reaction mixture may comprise products of Formula IX, although in other embodiments, products of Formula I can also be decarbonylated by a separate reaction in a separate reaction zone. Decarbonylation can be achieved in various ways. In one embodiment, it can be achieved by heating a process stream comprising the cyclic urea product(s) in water at elevated temperature, and optionally also elevated pressure. In other embodiments, it can be achieved by hydrolysis in the presence of a base such as sodium or potassium hydroxide, and optionally at elevated temperatures such as in the range of from 170 to 400° C., for example from 200 to 320° C.

In the process of the present invention, further products can form, for example through reaction of the cyclic alkylene urea product of Formula I with other components of the reaction zone, e.g. the existing reactants. This way, higher alkylene amines can be produced (optionally after decarbonylation). For example, the cyclic alkylene product of Formula I can react further to incorporate another alkyleneamine unit.

In embodiments, the desired products incorporate mixtures of compounds of Formula I in which p has multiple values, e.g. a mixture of 0, 1 and 2. As an example, if 2-oxazoline (CMEA) and/or ethanolamine (EA) are used as reactants of Formula II and/or Formula III, and ethylene urea (EU) and/or diethylamine (DEA) are used as reactants of Formula IV and/or Formula V, then products can include: 1-(2-aminoethyl)-imidazolidin-2-one (UDETA), the corresponding decarbonylated diethyltriamine (DETA), U-TETA, U1-TETA and U2-TETA (see FIG. 1) and 1,2-bis(ethyleneurea)ethane (DUTETA), which can be decarbonylated to form the corresponding triethyl-tetramine (TETA). This can then lead to higher amines (and equivalent compounds with urea (U) groups due to the carbonyl delivering compounds), e.g. tetraethylpentamine (TEPA), and pentaethylhexamine (HEPA).

The mixture of products can be separated by techniques such as distillation, optionally after decarbonylation. In embodiments, undesired products can be recycled to the reaction zone.

The invention will be elucidated by the following examples, without being limited thereto or thereby.

Experimental

In the Examples 1-4 below, ethylene diamine (EDA) and ethylene urea (EA) were added to a reaction vessel at room temperature and heated up to the specified reaction temperature. Ethanolamine (EA) or 2-oxazolidinone (CMEA) was then added either in a single dose, or in multiple batches. GC-FID (Gas Chromatography—Flame Ionisation Detection) was used to analyse the reaction mixture at various stages, and amounts are expressed in percent by weight unless specified otherwise.

Reactions were carried out using a Biotage Initiator+ microwave reactor using 5 ml Biotage glass vials, with stirring rods and caps. After addition of the reactants, the vials were flushed with nitrogen for two minutes, sealed and heated to reaction temperature.

At the end of the reaction, the reactors were cooled back to room temperature over a period of 3-4 minutes.

Example 1

2-Imidazolidinone (1.5 g, 17.42 mmol), Ethylenediamine (477 mg, 7.94 mmol), and 2-Aminoethanol (243 mg, 3.98 mmol) were added to a 5 ml vial. The vial was capped and flushed with N$_2$ before heating (over 2 minutes) to 250° C.

After 90 min, the vial was allowed to cool down to room temperature, and 2-Aminoethanol (243 mg, 3.98 mmol) was added. The vial was capped once more, flushed with Na heated back up to 250° C. for another 120 min before cool down to room temperature. A third addition of 2-Aminoethanol (243 mg, 3.98 mmol) was made to the reaction mixture. After capping and flushing with Na the reaction mixture was heated to 250° C. for a further 90 min before cool down to RT. The resulting reaction mixture was analyzed by GC-FID. Results are shown in Table 1.

Example 2

The procedure of Example 1 was followed, except that the vial was initially charged with Ethylenediamine (1.38 g, 22.96 mmol), 2-Imidazolidinone (515 mg, 5.98 mmol) and 2-Oxazolidinone (400 mg, 4.59 mmol), and at 90 minutes and 210 minutes additional charges of 2-Oxazolidinone (400 mg, 4.59 mmol) were added. The reaction mixture before each additional charge of 2-Oxazolidinone and at the end of the reaction was analysed by GC-FID. Results are shown in Tables 1 and 2.

Example 3 (Comparative)

A 5 mL microwave vial equipped with a magnetic stirring rod was charged with Ethylenediamine (1.38 g, 22.96 mmol), 2-Imidazolidinone (515 mg, 5.74 mmol) and 2-Oxazolidinone (1.2 g, 13.78 mmol). The vial was capped and flushed with Na, and heated to 250° C. over a period of 2 minutes using a Biotage Initiator+ microwave reactor. After 330 min, the reactor was cooled back down to room temperature, and the contents analysed by GC-FID. Results are shown in Table 1.

TABLE 1

Examples 1 and 2, and Comparative Example 3

| | Example: | | |
|---|---|---|---|
| | 1 | 2 | 3 |
| Total time (min) | 330 | 330 | 330 |
| Reactants (mole equivalents) | | | |
| EDA | 0.40 | 1.00 | 1.00 |
| EU | 0.85 | 0.25 | 0.25 |
| CMEA | 0 | 3 × 0.20 | 1 × 0.60 |
| MEA | 3 × 0.20 | 0 | 0 |
| CO:Amine mole ratio[1] | 0.68 | 0.68 | 0.68 |
| Reaction Mixture Composition (wt %) | | | |
| EDA | 20.6 | 17.4 | 21.8 |
| EU | 17.7 | 14.0 | 23.6 |
| MEA | 5.6 | 6.3 | 3.1 |
| CMEA | n.d. | n.d. | n.d. |
| AEEA | n.d. | 0.3 | 0.4 |
| UAEEA | 2.8 | 5.9 | 4.7 |
| UDETA | 26.8 | 25.1 | 21.7 |
| DETA | 1.9 | 1.8 | 1.4 |
| U2TETA | 0.9 | 0.9 | 0.9 |
| U1TETA | 1.7 | 3.3 | 1.2 |
| DUTETA | 4.8 | 6.0 | 5.5 |
| Σ(U)DETA + (U)TETAs[2,3] | 36.1 | 35.9 | 30.8 |
| [(C)MEA]/{[EU] + [EDA]}[4] | 0.16 | 0.16 | 0.48 |

[1]CO = EU + CMEA. Amine = EU + EDA. Based on total amount of material added to reaction zone
[2](U)DETA = sum of DETA and UDETA
[3](U)TETAs = sum of TETA, U1TETA, U2TETA and DUTETA
[4]Mole ratio of initial dose of MEA or CMEA to the combined amount of EU and EDA Compared to adding all the amount of MEA or CMEA at the beginning of the reaction, adding the same quantity of MEA or CMEA periodically in portions improves quantities of the desired higher alkyleneamine/cyclic alkylene urea products (i.e. Σ(U)DETA-P(U)TETAs).

Table 2 below shows the individual analyses just before each subsequent batch of CMEA was added.

TABLE 2

Results for Examples 2 and 3

| | Example | | | | |
|---|---|---|---|---|---|
| | 2&3 | 2 | 2 | 2 | 3 |
| No of CMEA additions | 0 | 1 | 2 | 3 | 1 |
| Time (min) | 0 | 90 | 210 | 330 | 330 |
| Temperature (° C.) | 250 | 250 | 250 | 250 | 250 |
| CO:Amine mole ratio[1] | 0.20 | 0.36 | 0.52 | 0.68 | 0.68 |
| Reaction Mixture Composition (wt %) | | | | | |
| EDA | 73.6 | 56.4 | 32.7 | 17.4 | 21.8 |
| EU | 26.4 | 17.7 | 15.9 | 14.0 | 23.6 |
| MEA | — | 13.4 | 11.3 | 6.3 | 3.1 |
| CMEA | — | n.d. | n.d. | n.d. | n.d. |
| AEEA | — | n.d. | n.d. | 0.3 | 0.4 |
| UAEEA | — | n.d. | 2.8 | 5.9 | 4.7 |
| UDETA | — | 1.6 | 14.3 | 25.1 | 21.7 |
| DETA | — | n.d. | 1.5 | 1.8 | 1.4 |
| U2TETA | — | n.d. | n.d. | 0.9 | 0.9 |
| U1TETA | — | n.d. | 0.6 | 3.3 | 1.2 |
| DUTETA | — | n.d. | 1.1 | 6.0 | 5.5 |
| Σ(U)DETA + (U)TETAs[2,3] | — | 1.6 | 17.5 | 35.9 | 30.8 |
| [(C)MEA]/{[EU] + [EDA]}[4] | — | 0.192 | 0.254 | 0.228 | 0.08 |

[1]CO = EU + CMEA. Amine = EU + EDA. Based on total amount of material added to reaction zone
[2](U)DETA = sum of DETA and UDETA
[3](U)TETAs = sum of TETA, U1TETA, U2TETA and DUTETA
[4]Mole ratio of (MEA + CMEA) to (EU + EDA) at time t, measured just before addition of next batch of CMEA or at end of experiment Example 4

The procedure according to Example 2 was followed, except that Ethylenediamine (2.00 g, 33.28 mmol), 2-Imidazolidinone (716 mg, 8.32 mmol) and 2-Oxazolidinone (580 mg, 6.66 mmol) were initially charged to the 5 ml vial, the reaction temperature was 260° C., and charges of 2-Oxazolidinone (580 mg, 6.66 mmol) were added as 90 minutes and 210 minutes. Results are shown in Table 3.

TABLE 3

Results for Example 4

| | No. CMEA additions | | | |
|---|---|---|---|---|
| | 0 | 1 | 2 | 3 |
| Time (min) | 0 | 90 | 210 | 330 |
| Temperature (° C.) | 260 | 260 | 260 | 260 |
| CO:Amine mole ratio[1] | 0.20 | 0.36 | 0.52 | 0.68 |
| Reaction Mixture Composition (wt %) | | | | |
| EDA | 73.6 | 45.8 | 30.3 | 18.8 |
| EU | 26.4 | 28.1 | 26.0 | 22.7 |
| MEA | — | 7.6 | 6.2 | 3.7 |
| CMEA | — | n.d. | n.d. | n.d. |
| AEEA | — | n.d. | n.d. | n.d. |

TABLE 3-continued

Results for Example 4

| | No. CMEA additions | | | |
|---|---|---|---|---|
| | 0 | 1 | 2 | 3 |
| 1. UAEEA | 2. — | 3. 0.5 | 4. 2.3 | 5. 3.4 |
| 6. UDETA | 7. — | 8. 6.3 | 9. 19.8 | 10. 28.1 |
| 11. DETA | 12. — | 13. 0.5 | 14. 1.4 | 15. 1.5 |
| 16. U2TETA | 17. — | 18. n.d. | 19. n.d. | 20. 0.7 |
| 21. U1TETA | 22. — | 23. n.d. | 24. 0.7 | 25. 1.4 |
| 26. DUTETA | 27. — | 28. n.d. | 29. 1.7 | 30. 5.1 |
| 31. E2U | 32. — | 33. 5.8 | 34. 4.1 | 35. 2.3 |
| Σ(U)DETAs + (U)TETAs[2,3] | — | 6.7 | 23.6 | 36.8 |
| [(C)MEA]/{[EU] + [EDA]}[4] | — | 0.114 | 0.126 | 0.105 |

[1]CO = EU + CMEA. Amine = EU + EDA. Based on total amount of material added to reaction zone
[2](U)DETA = sum of DETA and UDETA
[3](U)TETAs = sum of TETA, U1TETA, U2TETA and DUTETA
[4]Mole ratio of (MEA + CMEA) to (EU + EDA) at time t, measured just before addition of next batch of CMEA or at end of experiment These results further confirm that maintaining low (C)MEA to EU+ EDA mole ratios, by controlling how much is added at any one time, is beneficial to achieving higher cyclic alkylene urea product yields, which would also result in improved higher alkylene amine yields after decarbonylation.

Example 5

In this example, 2-oxazolidinone (CMEA) and 1-(2-aminoethyl)-2-imidazolidinone (UDETA) were added to a reaction vessel at room temperature. Subsequently, the vessel was heated up to the specified reaction temperature. CMEA (2-oxazolidinone) was added either in a single dose, or in multiple batches. GC-FID (Gas Chromatography—Flame Ionisation Detection) was used to analyse the reaction mixture at various stages.

Reactions were carried out using a Biotage Initiator+ microwave reactor using 5 ml Biotage glass vials, with stirring rods and caps. After addition of the reactants, the vials were flushed with nitrogen for two minutes, sealed and heated to reaction temperature.

At the end of the reaction, the reactors were cooled back to room temperature over a period of 3-4 minutes.

Results

Two experiments were done. Experiment 5B is comparative.

In experiment 5A, 2-oxazolidinone (CMEA) and 1-(2-aminoethyl)-2-imidazolidinone (UDETA) were mixed in a mole ratio of 0.4:1. This mixture, with a total mass of 2.39 grams was added to a 5 ml vial. After reaction at 280° C. for 1 hour, 0.4 mole equivalents of 2-oxazolidinone (CMEA) was added and the mixture was reacted at 280° C. for 1 additional hour. This was repeated three more times. After a total reaction time of 5 hours the sample was analyzed by GC-FID (Gas Chromatography—Flame Ionisation Detection) and the results are shown in Table 4.

In experiment 5B, 2-oxazolidinone (CMEA) and 1-(2-aminoethyl)-2-imidazolidinone (UDETA) were mixed in a mole ratio of 2:1. This mixture with a total mass of 4.41 grams was added to a 5 ml vial. After a total reaction time of 3 hours the sample was analyzed by GC-FID (Gas Chromatography—Flame Ionisation Detection) and the results are shown in Table 4.

TABLE 4 results of example 5

| | Experiment | |
|---|---|---|
| | 5A | 5B |
| Temperature | 280° C. | 280° C. |
| Reaction time | 5 h | 5 h |
| Dosing | 4 additions of CMEA | CMEA added all at once |
| Relative Yield (%) | | |
| (U)AEEA | 30% | 20% |
| (U)TETA | 45% | 33% |
| (U)TEPA | 14% | 16% |

(U)AEEA = sum of AEEA and UAEEA
(U)TETA = sum of TETA and UTETA compounds
(U)TEPA = sum of TEPA and U-TEPA compounds These results further confirm that maintaining low (C)MEA to UDETA mole ratios, by controlling how much is added at any one time, is beneficial to achieving higher cyclic alkylene urea product yields, which would also result in improved higher alkylene amine yields after decarbonylation.

Example 6

In this example, ethylene diamine (EDA) and ethylene urea (EA) were added to a reaction vessel at room temperature and heated up to the specified reaction temperature. Ethanolamine (EA) or 2-oxazolidinone (CMEA) was then added either in a single dose, or in multiple batches. GC-FID (Gas Chromatography—Flame Ionisation Detection) was used to analyse the reaction mixture at various stages, and amounts are expressed in percent by weight unless specified otherwise.

Reactions were carried out using a Biotage Initiator+ microwave reactor using 5 ml Biotage glass vials, with stirring rods and caps. After addition of the reactants, the vials were flushed with nitrogen for two minutes, sealed and heated to reaction temperature.

At the end of the reaction, the reactors were cooled back to room temperature over a period of 3-4 minutes.

Results

Two experiments were done of which experiment 6B is comparative.

In experiment 6A, 2-oxazolidinone (CMEA), ethylene diamine (EDA) and 2-imidazolidinone (EU) were mixed in a mole ratio of 1:1.5:1. This mixture with a total mass of 3.628 grams was added to a 5 ml vial. After reaction at 260° C. for 1 hour, 0.4 mole equivalents of 2-oxazolidinone (CMEA) was added and the mixture was reacted at 260° C. for 1 additional hour. Then, 0.4 mole equivalents of 2-oxazolidinone (CMEA) was added and the mixture was reacted at 260° C. for 1 additional hour.

After a total reaction time of 3 hours the sample was analyzed by GC-FID (Gas Chromatography—Flame Ionisation Detection) and the results are shown in Table 5.

In experiment 6B, 2-oxazolidinone (CMEA), ethylene diamine (EDA) and 2-imidazolidinone (EU) were mixed in a mole ratio of 1.8:1.5:1. This mixture with a total mass of 4.2 grams was added to a 5 ml vial. After a total reaction time of 3 hours the sample was analyzed by GC-FID (Gas Chromatography—Flame Ionisation Detection) and the results are shown in Table 2.

TABLE 2

|  | Experiments | |
| --- | --- | --- |
|  | 2A | 2B |
| Temperature | 260° C. | 260° C. |
| Reaction time | 3 h | 3 h |
| Dosing | 2 additions of CMEA | CMEA added all at once |
| Relative Yield (%) | | |
| (U)TETA | 36% | 32% |
| (U)DETA | 43% | 33% |
| (U)AEEA | 20% | 35% |
| (U)TEPA | 1% | 0% |

(U)TETA = sum of TETA and UTETA compounds
(U)AEEA = sum of AEEA and UAEEA
(U)DETA = sum of DETA and UDETA
(U)TEPA = sum of TEPA and U-TEPA compounds These results further confirm that maintaining low (C)MEA to EU+ EDA mole ratios, by controlling how much is added at any one time, is beneficial to achieving higher cyclic alkylene urea product yields, which would also result in improved higher alkylene amine yields after decarbonylation.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

Abbreviations Used

AEEA aminoethylethanolamine, or 2-[(2-aminoethyl)amino]ethanol
CMEA 1,3-oxazolidin-2-one or 2-oxazolidinone
DETA diethylenetriamine, or N-(2-aminoethyl)-1,2-ethanediamine
DUTETA 1,2-bis(ethyleneurea)ethane or 1,1'-(1,2-ethanediyl)di(2-imidazolidinone)
DUTEPA tetraethylenepentamine containing two cyclic urea groups—see FIG. 1
EDA ethylenediamine, or 1,2-diaminoethane
E2U 1,3-diethylurea
EU ethyleneurea, or 2-imidazolidinone
MEA ethanolamine, or 2-aminoethanol
PEHA pentaethylenehexamine
PIP piperazine
TEPA tetraethylenepentamine
TETA triethylenetetramine (L-TETA refers specifically to linear-TETA)
UAEEA N-(2-hydroxyethyl)-ethyleneurea, or 1-(2-hydroxyethyl)-imidazolidin-2-one
UDETA N-(2-hydroxyethyl)-ethyleneurea, or 1-(2-aminoethyl)-imidazolidin-2-one
UTETA TETA containing a cyclic urea group—See FIG. 1
U1TETA UTETA with the cyclic urea group on one end of the molecule—See FIG. 1
U2TETA UTETA with the cyclic urea group in the centre of the molecule—See FIG. 1

What is claimed is:

1. A process for producing 1-(2-aminoethyl) imidazolidin-2-one (UDETA), the process comprising:
   contacting 2-oxazolidinone (CMEA) and/or monoethanolamine (MEA) in a reaction zone with ethyleneurea (EU) and/or ethylenediamine (EDA) and in the presence of one or more carbonyl delivering compounds;
   wherein the ethyleneurea (EU) and/or the ethylenediamine (EDA) is present in a reaction zone, and wherein the 2-oxazolidinone (CMEA) and/or the monoethanolamine (MEA) are added to the reaction zone semi-continuously or in two or more batches.

2. The process of claim 1, wherein the 2-oxazolidinone (CMEA) and/or the monoethanolamine (MEA) are added to the reaction zone semi-continuously.

3. The process of claim 1, wherein the 2-oxazolidinone (CMEA) and/or the monoethanolamine (MEA) are added to the reaction zone in two or more batches.

4. The process of claim 1, further comprising limiting an amount of CMEA and MEA and EU and EDA in the reaction zone to a predetermined molar ratio of CMEA and MEA to EU and EDA, wherein the predetermined molar ratio is 0.60:1.

5. The process of claim 1, further comprising limiting an amount of CMEA and MEA and EU and EDA in the reaction zone to a predetermined molar ratio of CMEA and MEA to EU and EDA, wherein the predetermined molar ratio is 0.30:1.

6. The process of claim 1, further comprising limiting an amount of CM EA and MEA and EU and EDA in the reaction zone to a predetermined molar ratio of CMEA and MEA to EU and EDA, wherein the predetermined molar ration is 0.25:1.

7. The process of claim 1, further comprising limiting an amount of CM EA and MEA and EU and EDA in the reaction zone to a predetermined molar ratio of CMEA and MEA to EU and EDA, wherein the predetermined molar ration is 0.20:1.

8. The process of claim 1, further comprising limiting an amount of CM EA and MEA and EU and EDA in the reaction zone to a predetermined molar ratio of CMEA and MEA to EU and EDA, wherein the predetermined molar ration is 0.16:1.

9. The process of claim 1, wherein the carbonyl delivering compound is selected from carbon dioxide; inorganic carbonic acid salts; cyclic and non-cyclic carbonic acid esters; urea; optionally substituted alkyl ureas; optionally substituted cyclic alkylene ureas; carbamic acids; carbamic acid salts; and cyclic and non-cyclic carbamic acid esters.

10. The process of claim 1, wherein the carbonyl delivering compound is selected from 2-oxazolidinone (CMEA) and ethylenediamine (EDA).

* * * * *